US009322775B2

(12) United States Patent
Gagliardi et al.

(10) Patent No.: US 9,322,775 B2
(45) Date of Patent: Apr. 26, 2016

(54) FREQUENCY COMB SPECTROSCOPY APPARATUS AND METHOD OF FREQUENCY COMB SPECTROSCOPY

(71) Applicant: CNR—CONSIGLIO NAZIONALE DELLE RICERCHE, Rome (IT)

(72) Inventors: Gianluca Gagliardi, Florence (IT); Saverio Avino, Florence (IT); Antonio Giorgini, Florence (IT); Paolo De Natale, Florence (IT)

(73) Assignee: CNR—CONSIGLIO NAZIONALE DELLE RICERCHE, Rome (IT)

( * ) Notice: Subject to any disclaimer, the term of this patent is extended or adjusted under 35 U.S.C. 154(b) by 0 days.

(21) Appl. No.: 14/758,233

(22) PCT Filed: Dec. 28, 2012

(86) PCT No.: PCT/IB2012/057796
§ 371 (c)(1),
(2) Date: Jun. 27, 2015

(87) PCT Pub. No.: WO2014/102572
PCT Pub. Date: Jul. 3, 2014

(65) Prior Publication Data
US 2015/0355086 A1   Dec. 10, 2015

(51) Int. Cl.
| G01J 3/28 | (2006.01) |
| G01N 21/39 | (2006.01) |
| G01J 3/02 | (2006.01) |
| G01J 3/433 | (2006.01) |

(52) U.S. Cl.
CPC . *G01N 21/39* (2013.01); *G01J 3/02* (2013.01); *G01J 3/0218* (2013.01); *G01J 3/28* (2013.01); *G01J 3/2803* (2013.01); *G01J 2003/4332* (2013.01); *G01N 2021/391* (2013.01); *G01N 2021/399* (2013.01); *G01N 2201/06113* (2013.01); *G01N 2201/08* (2013.01)

(58) Field of Classification Search
CPC ................. G01J 3/02; G01J 3/10; G01J 3/28; G01J 3/2803; G01J 3/2823; G01N 21/39
USPC ................................................. 356/300–334
See application file for complete search history.

(56) References Cited

U.S. PATENT DOCUMENTS

| 8,120,773 B2 | 2/2012 | Gohle et al. | |
| 2008/0074660 A1 | 3/2008 | Ye et al. | |
| 2012/0133931 A1* | 5/2012 | Fermann | G01J 3/10 356/300 |

OTHER PUBLICATIONS

J.Ye and S.T. Cundiff "Femtosecond optical frequency comb technology: principle, operation and application" (Springer, New York, 2005).
T. Gherman and D. Romanini "Mode-locked cavity-enhanced absorption spectroscopy" Optic Express vol. 10, n° 19, pp. 1033-1042 (2002).
von Lerber T., Sigrist M. W. "Cavity-ring-down principle for fiber-optic resonators: experimental realization of bending loss and evanescent-field sensing." Appl. Opt. 41, 3567-3575 (2002).
M.J. Thorpe et al. "Broadband cavity ringdown spectroscopy for sensitive and rapid molecular detection", Science 311, 1595-1599 (2006).
G. Gagliardi et al: "Optical-frequency-comb based interrogation of fiber resonators", Proceedings of SPIE, vol. 7753, May 15, 2011, pp. 775311-1-775311-4.

* cited by examiner

*Primary Examiner* — Abdullahi Nur
(74) *Attorney, Agent, or Firm* — Volpe and Koenig, P.C.

(57) ABSTRACT

The present invention relates to a method and an apparatus to perform frequency comb spectroscopy. The method includes: —Arranging a waveguide optical cavity (3) having a plurality of cavity mode frequencies with a cavity mode frequency spacing (FSR), said waveguide optical cavity being dispersive so that the frequency spacing of the cavity modes is wavelength dependent; —Arranging a sample (S) with respect to the waveguide optical cavity (3) so that the sample is capable of absorbing light travelling into the waveguide optical cavity; —Coupling pulsed light coming from a light source (1) into the waveguide optical cavity (3), the source light including source comb frequencies (OCF) with a source frequency spacing (RR), the coupled light including an interval of frequencies centered on a main frequency of said comb frequencies due to cavity dispersion; —Locking the waveguide optical cavity to the frequency comb at said main optical frequency; —Detecting transmitted cavity frequencies; —Determining absorption by said sample (S) of said main optical frequency from the detected transmitted frequencies, —Changing the cavity mode frequency (FSR) spacing or the source frequency spacing (RR); —Coupling the pulse light to the waveguide optical cavity (3), the coupled light including an interval of frequencies centered on a second main frequency of said comb frequencies due to cavity dispersion; —Locking the waveguide optical cavity to the frequency comb at said second main optical frequency; —Detecting transmitted cavity frequencies; —Determining absorption by said sample of said second main optical frequency from the detected transmitted frequencies.

17 Claims, 8 Drawing Sheets

FREQUENCY COMB SPECTROSCOPY APPARATUS AND METHOD OF FREQUENCY COMB SPECTROSCOPY

TECHNICAL FIELD

The present invention relates to an apparatus for performing frequency comb spectroscopy and a method to perform frequency comb spectroscopy. The apparatus and the method are designed in order to achieve sensitive and relatively simple measurements, in particular for liquid samples.

BACKGROUND ART

Laser spectroscopy is currently enabling a large number of experiment for scientific investigation. The development of new spectroscopic method and apparatuses is still in progress, to always obtain better monitoring and precise quantitative measurements of the physical world.

Optical frequency combs (OFCs) led to impressive advances in the field of metrology and fundamental physics as detailed for example in J. Ye and S. T. Cundiff "*Femtosecond optical frequency comb technology: principle, operation and application*" (Springer, New York, 2005). In addition, OFCs have been proposed for a number of different applications, such as characterization of dispersion in optical materials, absolute length measurements, strain sensing, cavity-enhanced and Fourier Transform molecular spectroscopy.

Optical resonator-based detection methods, either realized with conventional mirror cavities or optical fibers and waveguides, have demonstrated a huge potential in spectroscopic and sensing applications such as in T. Gherman and D. Romanini "*Mode-locked cavity-enhanced absorption spectroscopy*" Optic Express Vol. 10, n° 19, pages 1033-1042 (2002).

In this field, a major breakthrough was represented by coherent coupling of OFCs to high finesse cavities used as sample chambers. Spectral analysis of the light transmitted by the cavity can be performed by dispersive elements to extract the absorption features over several tens of nm. Such systems exploit the intrinsic advantages of comb lasers, i.e. wide spectral coverage with a multi-wavelength coherent source and metrological-grade frequency stability, while preserving the intrinsic sensitivity of cavity-enhanced methods. Nevertheless, comb-based absorption spectrometers have rested on conventional linear cavities and used only for spectroscopy in the gas phase.

So far, there have been only a few works on absorption spectroscopy in the liquid phase. Liquid spectroscopy has a huge potential for analysis of many species in the liquid phase, e.g. in environmental pollution and industrial process monitoring as well as food safety control and biomedical analysis. Common cavity enhanced techniques, originally developed for gas spectroscopy, present well-known drawbacks when extended to liquid compounds. For instance, introduction of liquids in a high reflectivity mirror cavity directly or by means of an intracavity couvette causes a significant loss increase and additional reflections. An alternative and minimally-invasive method, is the use of total internal reflection at the interface between two media with different dielectric constants. For instance, in optical waveguide resonators, the interaction with liquid chemicals in the surrounding environment may occur if the internal evanescent field is exposed along the cavity-medium interface, as discussed in von Lerber T., Sigrist M. W. "*Cavity-ring-down principle for fiber-optic resonators: experimental realization of bending loss and evanescent-field sensing.*" *Appl. Opt.* 41, 3567-3575 (2002). In fiber-optic resonators, this is possible by creating a side-polished region where the external cladding is removed while the total internal reflection condition is still satisfied. A change in ambient refractive index leads to a wavelength shift of the cavity modes and may increase the penetration depth of the evanescent-wave tail. On the other hand, if the interacting molecules exhibit optical absorption features in the vicinity of the resonance, the lifetime of photons within the cavity is reduced as a consequence of loss increase. The use of optical fiber evanescent-wave sensors has several advantages. They are particular suitable for in-situ, non-invasive sensing, and they can be used both in hardly-accessible and harsh environments even in remote operation. Additionally, fiber optic based resonators are cheap, compact, easy to build and do not require special care in terms of alignment, cleaning and isolation.

In the work of M. J. Thorpe et al. "*Broadband cavity ringdown spectroscopy for sensitive and rapid molecular detection*", Science 311, 1595-1599 (2006) a femtosecond pulse train generated with a mode-locked laser source is coupled into a resonator cavity including a sample to be investigated. The femtosecond pulse train and the resonator cavity are tuned such that the cavity modes essentially corresponds to the comb components of the femtosecond pulse train. Due to the large number of round trips within the cavity, the interaction of the sample with light is essentially increased. Absorption profiles are measured by using the cavity ringdown technique. The comb beam is switched off through an acusto-optical modulator (AOM). The light transmitted through the cavity is spectrally resolved and detected via a CCD camera. For measuring the ring down exponential decays, a scanning mirror is used for streaking the spectrally resolved light pulses into different portions of the sensitive area of the CCD sensor.

U.S. Pat. No. 8,120,773 discloses a spectroscopic analysis of a sample which includes arranging the sample in a resonator cavity for transmitting cavity mode frequencies with a cavity mode frequency spacing, coupling pulsed source light into the resonator cavity, with the source light including source comb frequencies with a source frequency spacing, coupling pulsed transmitted light out of the resonator cavity, and spectrally resolved detecting the transmitted light with a detector device. The cavity mode frequency spacing and the source frequency spacing are detuned relative to each other, so that the transmitted light includes transmitted comb frequencies with a spacing larger than the source frequency spacing. The detecting feature includes collecting spectral distributions of the transmitted light in dependence on relative positions of the cavity mode frequencies and the source comb frequencies. The cavity mode frequencies and the source comb frequencies are varied relative to each other and different transmitted comb frequencies are individually resolved.

SUMMARY OF THE INVENTION

The present invention relates to a method and to an apparatus for frequency comb spectroscopy of a given sample. More in detail, the invention is relative to cavity enhanced spectroscopy, which efficiently couples a broadband optical frequency comb to a high finesse optical cavity inside which a sample test is placed. The output of the optical cavity is a multiplicity of channels of data resulting from the differential absorption of light at various comb frequencies. Preferably, the device can operate in a ringdown mode or a non-ringdown enhanced absorption spectroscopy mode. Careful measurement and control of cavity dispersion and comb spacing are part of the coupling process.

To perform spectroscopy of the given sample, an optical frequency comb light source is used.

In the following, the term "light" will be used as a synonym of the term "electromagnetic radiation", therefore a light impulse does not mean that it consists of visible radiation only. On the contrary, "light" might include visible radiation and/or non-visible radiation.

Figure 1:
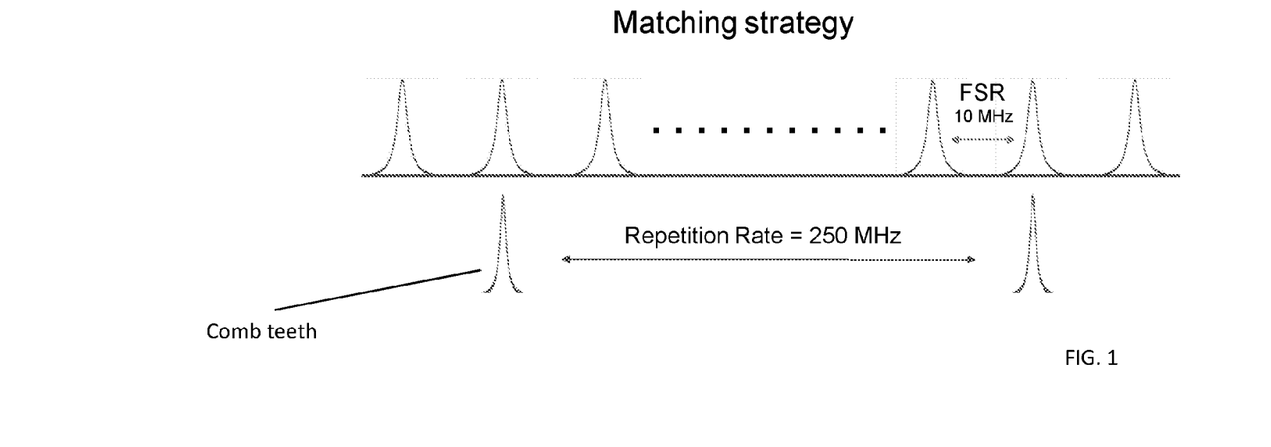
FIG. 1 is a schematic representation of a step of the method of the invention.

An optical frequency comb is a light source whose frequency spectrum consists of equidistant in phase coherent teeth (see FIG. 1). Therefore a light source capable of emitting pulsed light including comb frequencies means that the source is such that it can emit, in the frequency space, a plurality of frequency components which can be written as (in an ideal case)

$$v(n) = nf_r + f_0 \tag{1}$$

where n is an integer mode number, $f_r$ is the comb line spacing also called repetition rate (RR) and $f_0$ is the carrier offset frequency. The frequency components of the source light are called "source comb frequencies" and the difference between two adjacent frequencies is called "comb frequency spacing". Preferably, the frequency spacing is comprised between 100 MHz and tens of GHz.

In the time domain, the source is emitting short light pulses, e.g. pulses having preferably a pulse duration from tens of femtoseconds to tens of picoseconds.

The light source is selected in dependence of the spectral range to be investigated. Preferably, the light source includes a laser. According to a preferred embodiment, the light pulses are generated stabilizing the pulse train of a mode locked laser. However different sources can be used as well. The sample to be investigated according to the invention by the above defined light source is in optical coupling with an optical waveguide cavity.

In general, an optical cavity, also called optical resonator or resonant optical cavity, is an arrangement of optical components which allows a beam of light to circulate in a closed path. Such resonators can be made in very different forms, for example they can be realized using refractive mirrors or waveguides. An optical waveguide cavity is in the present invention an optical cavity formed using a waveguide.

In the present invention, the optical waveguide cavity includes a waveguide to which and from which light can be coupled. In particular, the light coming from the above defined light source can be coupled as well. The light can travel within the waveguide. Preferably, the cavity is a single mode cavity. In the optical waveguide cavity, resonator modes are the modes of the optical resonator, i.e. field distributions which reproduce themselves (apart from a possible loss of power) after one round trip. For each of the transverse mode patterns, there are only certain optical frequencies for which the optical phase is self-consistently reproduced after each round trip (i.e. the round-trip phase shift is an integer multiple of 2 π). These are called the mode frequencies or resonance frequencies and are approximately equidistant. The frequency spacing of the resonator modes, also called free spectral range (FSR), is called in the following "resonator frequency spacing" and it only depends on the resonator length: FSR=c/2 nL where L is the length of the resonator, c the speed of light and n the effective index of refraction of the waveguide. The ratio of the frequency spacing to the width of the resonances (resonator bandwidth) is called the finesse and is determined by the power losses per resonator round trip. A related measure is the Q factor, which is the ratio of resonance frequency and bandwidth. Preferably, the optical resonator waveguide includes a resonator loop waveguide. For a waveguide loop, the resonant modes are those which satisfy the following resonant condition:

$$m\lambda_m = L\, n_{eff} \tag{2}$$

Where $\lambda_m$ is the resonant wavelength and m is an integer mode number of the resonator, L is the length of the loop resonator and $n_{eff}$ is the effective index of refraction of the waveguide material.

The term "sample" in the following refers to any gaseous, liquid or solid substance being capable of being arranged in light coupling with the resonant cavity. Being in light coupling means that the modes travelling within the cavity interact with the sample itself. The interaction can be for example through the evanescent field of the travelling modes, however other interactions are included in the invention as well. Preferably, the sample includes a liquid sample.

It is desired to analyze the sample, i.e. to perform spectroscopy of the sample, which is in optical interaction with the cavity. These interactions include absorption, which occurs when energy from the light source is absorbed by the sample. Absorption is determined by measuring the fraction of energy transmitted through the sample; absorption will decrease the transmitted portion.

In the present case, the transmitted light from the sample is analyzed in order to ascertain its properties.

The term "transmitted light" refers to the light pulses coupled out of the resonator optical cavity. The transmitted light is generally represented by a frequency comb containing information of the sample's spectrum. Each transmitted light comb represents a group of transmitted light frequencies. The light exiting the cavity is affected by the sample such that certain frequencies are absorbed, as detailed below.

In standard comb spectroscopy, for example in a system where the cavity is realized using mirrors, when many comb frequencies are coupled to the cavity, the absorption of light at each frequency by the sample has to be determined. In other words, the transmitted light, which includes a vast plurality of different "peaks", has to be individually resolved in order to measure the spectral structure of the sample. This generally requires a plurality of detectors and dispersive elements which increases the complexity and the dimensions of the overall apparatus. Moreover, the various frequencies have to be spatially separated in order to obtain the desired information.

Applicants have realized that, using a generally "unwanted" characteristic of waveguides, i.e. their dispersion, greatly simplify the situation. The plurality of transmitted "peaks" is greatly reduced, due to the fact that only a very small interval of frequencies of the comb is coupled to the cavity. In particular, preferably, the number of transmitted frequencies can be reduced to a number which does not have to be resolved any more, i.e. the resulting transmitted number of different peaks lies within the desired resolution, therefore a single detector is enough.

In other words, the intrinsic dispersion of the fiber reduces the number of peaks to a level which does not require further analysis or resolution, limiting the number of detector or filter required to analyze the transmitted light. Intracavity dispersion, an unavoidable shortcoming of previous systems, is exploited in the present invention for spectroscopic analysis of absorption signals without using any fixed or movable dispersive element. The waveguide cavity behaves as an intrinsically tunable disperser allowing only a narrow window of the comb spectrum to be resonant in the cavity itself.

In order to obtain the whole spectrum of the transmitted light from the sample, the interval of frequencies which is transmitted should be changed in order to "scan" the possible spectrum.

Due to fiber's dispersion, the comb frequencies coupled to the cavity lie within a given interval around a "primary comb resonance" (also called in the following main or central frequency) which is called in the following $\omega_0$. This primary comb resonance depends, among others, on the comb repetition rate, therefore changing the repetition rate of the comb changes the transmitted frequencies' interval, i.e. it changes $\omega_0$. Alternatively, the length of the cavity can be changed in order to change $\omega_0$.

Changing the relative spacing of the source comb frequencies and/or cavity mode frequencies yields different transmitted comb frequencies. Groups of different transmitted comb frequencies yield characteristic spectral distribution, which are collected with a detector device.

In this way the whole spectrum is "scanned", obtaining a transmitted spectrum of the sample at various frequencies, one at the time, thus obtaining an absorption spectrum of the sample.

According to a first aspect, the invention relates to a method to perform frequency comb spectroscopy, including:
- Arranging a waveguide optical cavity having a plurality of cavity mode frequencies with a cavity mode frequency spacing, said waveguide optical cavity being dispersive so that said frequency spacing of the cavity modes is wavelength dependent;
- Arranging a sample with respect to the cavity so that the sample is capable of absorbing light travelling into the optical cavity;
- Coupling pulsed light coming from a light source into the waveguide optical cavity, the source light including source comb frequencies with a source frequency spacing, the coupled light including an interval of frequencies centered on a main frequency of said comb frequencies due to cavity dispersion;
- Locking the waveguide optical cavity to the frequency comb at said main optical frequency;
- Detecting transmitted cavity frequencies;
- Determining absorption by said sample of said main optical frequency from the detected transmitted frequencies;
- Changing the cavity mode frequency spacing or the source frequency spacing;
- Coupling the pulse light to the waveguide optical cavity, the coupled light including an interval of frequencies centered on a second main frequency of said comb frequencies due to cavity dispersion;
- Locking the frequency comb to the waveguide optical cavity at said second main optical frequency;
- Detecting transmitted cavity frequencies;
- Determining absorption by said sample of said second main optical frequency from the detected transmitted frequencies.

According to a second aspect, the invention relates to an apparatus for frequency comb spectroscopy, including:
- a waveguide optical cavity having a plurality of cavity mode frequencies with a cavity mode frequency spacing, said waveguide optical cavity being dispersive so that said frequency spacing of the cavity modes is wavelength dependent;
- a sample arranged with respect to the waveguide optical cavity so that the sample is capable of absorbing light travelling into the waveguide optical cavity;
- a light source capable of emitting source comb frequencies with a source frequency spacing;
- coupling means to couple the source comb frequencies to the waveguide optical cavity, the coupled light including an interval of frequencies centered on a main frequency of said comb frequencies due to cavity dispersion;
- a locking device to lock the waveguide optical cavity to the frequency comb at said main optical frequency;
- a detector for detecting transmitted cavity frequencies and determining absorption by said sample of said main optical frequency from the detected transmitted frequencies;
- a tuner to change the cavity mode frequency spacing or the source frequency spacing.

It is known that the coupling of the optical comb to the resonator is obtained when the "magic condition" is satisfied $$f_r = m \, FSR, \quad (3)$$

where m is an integer, which is also called the magic number. When such a condition is satisfied, the comb frequencies correspond to the resonator modes and this is ideally true for all comb frequencies.

In order to avoid power loss from the source, the spacing of the cavity mode frequencies is preferably equal or smaller than the spacing between the comb frequencies.

It is known that eq. (1) cannot be satisfied for a "very big" number of frequencies, due to cavity dispersion. For example, for a loop resonator cavity, the matching rule of eq. (1) becomes $$f_r = m \, FSR = m \frac{c}{nL}$$

(4) where m is an integer, i.e. the magic number, c is speed of light in vacuum, L is the loop length and n is the fiber refractive index. For an "ideal" cavity the matching is for an "infinite" number of frequencies (i.e. for an infinite number of integer m).

Generally, the cavities used in optical comb spectroscopy are realized using dispersion compensated mirrors. Although the cavity dispersion in these resonant cavity is not very high in absolute figures, it anyhow limits the comb bandwidth that can be coupled to the cavity modes. Several techniques have been developed in the prior art, such as in U.S. Pat. No. 7,538,881, to overcome the non-constant FSR of the cavity resonant frequencies.

A waveguide resonator however, either in the form of a cavity or a loop, has a given dispersion which is in general much higher (e.g. preferably at least 100 times higher) than the dispersion of a resonator realized using reflecting mirrors. The effect of the dispersion onto the cavity modes is that the frequency spacing of the cavity modes becomes wavelength dependent, e.g. the FSR becomes wavelength dependent. The effect of the dispersion is therefore that the spectral bandwidth of the frequency comb that can be coupled into the optical cavity, as it will be better described below, is limited.

In other words, the dispersion of the waveguide, which is always present, does not allow a coupling of "many" comb frequencies to the resonator modes. Hence the cavity itself acts as an intrinsic "fiber dispersion spectrometer" thus providing a direct spectral analysis of the intracavity absorption signals.

Preferably the waveguide cavity is a single mode cavity.

Preferably, the minimum dispersion of the waveguide cavity is defined as follow. Considering the group velocity dispersion (GVD), which causes a short pulse of light to spread in time as a result of different frequency components of the pulse travelling at different velocities within the waveguide, the waveguide cavity of the invention should have a GVD of at least 0.0074 ps$^2$/m at the resonant wavelength which, in the embodiment of the present invention, would corresponds to a resolution of 5 nm. The waveguide cavities of the present invention preferably includes a waveguide having a GVD bigger or equal to 0.0074 ps$^2$/m at the wavelength of interest.

Applicants have therefore considered to use this normally acknowledged as "disadvantage" of fibers, as a positive characteristic in order to perform spectroscopy of the sample. Indeed the method of the invention includes to set the repetition frequency or the FSR of the spectroscopy apparatus in such a way that instead of coupling and analysing the entire spectrum of the comb at the same time, only a narrow interval around a "central or main frequency" is considered at a time. More in detail, to make the optical frequency comb resonating with the fiber loop, preferably the repetition rate is tuned in order to match the magic condition of eq. (1) for the cavity, which is achieved when the comb teeth spacing is an integer multiple of the cavity FSR for a certain wavelength. However, the fiber cavity acts as a dispersive element, i.e. a fiber dispersion spectrometer. Therefore, for different wavelengths, the magic condition is satisfied by a slightly different repetition rate.

The result is that the matching between the cavity modes and the comb frequencies, due to fibre's dispersion, is such that only a very narrow band of comb frequencies, according to the invention only an interval of frequencies around the central main frequency, is allowed to resonate within the resonator. This is automatically due to the fibres' dispersion, no additional element is required to be present in the apparatus, i.e. the resonator acts as a dispersive element by itself.

The interval of frequencies of the comb which is matched to the waveguide cavity can include preferably about one hundred (or of the order of hundred) frequencies, centered in what has been called the "main frequency". For the spectroscopy of liquid samples, this is within the desired resolution: absorption bands of liquids have linewidths of the order of tens of nanometers, therefore a resolution of the order of nanometer is reasonable, which is the resolution obtained matching about 100 comb frequencies. Thus obtaining a resolution of about a fraction of a nm gives the desired resolution and there is no need of additional filters to resolve these lines.

The number of coupled frequencies, i.e. the width of the coupled interval, indeed can be changed depending on the desired resolution to be achieved. The number of frequencies coupled depends on the dispersion: the higher the dispersion, the smaller the number of coupled frequencies (the width of the coupled interval becomes smaller) and the higher the resolution.

With a given interval of frequencies around the so called "main frequency", a line of the spectrum of the sample is obtained detecting the transmitted light from the sample. Measuring the absorbed frequencies of the transmitted cavity light yields a spectrum line. Therefore, in order to obtain a complete analysis of the sample, the main frequency is changed, so another interval of frequencies—centered on another main central frequency—is coupled to the waveguide cavity.

In order to modify the main frequency, either the resonator or the source is adjusted so that a different comb frequency can resonate within the resonator, i.e. a new comb frequency "interval" cantered on a new main frequency is coupled to the cavity. Generally, the main frequency is changed and the width of the interval around it remains the same, so the same number of frequencies of the comb are coupled to the cavity. Therefore different intervals of the comb frequency spectrum are coupled to the cavity so that all frequencies are "in chunks" coupled to the cavity.

Preferably, the central operating wavelength resonating in the cavity is then swept by tuning the repetition rate. "Scanning" all the frequencies of interest within a given bandwidth, and detecting the corresponding signal from the sample, which is the outcome of the absorption of that selected wavelength from the same, the entire bandwidth of interest is sampled, one comb component (or very few components as above said, "interval" of frequencies within the desired resolution are coupled) at a time successively.

Preferably, the light source emits light in the near infrared region.

Preferably the locking of the fiber loop cavity to the comb laser is obtained using the Pound-Drever-Hall (PDH) technique.

Preferably, the investigated sample is a liquid sample.

Preferably, the cavity is a waveguide loop cavity. More preferably, it includes a single mode optical fiber. Multiple round-trips in fiber-optic resonators provide a longer effective absorption path-length and thus stronger signals. At the same time, the possibility to devise analyzers whose sensitive element acts as a separate probe, eventually in remote operation, is highly desirable for liquid sensing. Optical fibers are particularly suitable for in-situ, non-invasive sensing, even in hardly-accessible environments, and lend themselves to the realization of multiplexed chemical probes. Furthermore, fiber-optic resonators are cheap, compact, easy to build and they do not require special care in terms of alignment, cleaning and isolation.

Preferably, the spectroscopy method of the invention is used to perform cavity ring-down spectroscopy.

In ring-down spectroscopy, when the comb is coupled to the cavity, the source is then turned off in order to allow the measurements of the exponentially decaying light intensity leaking from the cavity. During the decay, the light has a very long effective path length for the extinction. Due to the presence of the sample, which absorbs light, the amount of light decreases faster before extinction than in a configuration without sample. A cavity ring down absorption method includes a step of measuring how long it takes for light to decay 1/e of its initial intensity, and this "ringdown time" is used to calculate the concentration of the absorbing substance in the cavity.

As said above, the coupled frequencies in the waveguide are a "main" frequency "surrounded" by a plurality of additional frequencies. The width of this frequency interval depends on the fiber's dispersion. The additional frequencies are called in the following "secondary frequencies". Applicants have noted that, examining the reflected light from the resonator cavity, the "secondary magic conditions" frequencies are narrower with respect to the peak visible at the "main magic condition" (i.e. the main frequency). This behavior, i.e. the fact that the additional resonances to the central frequency are narrower and also have a smaller intensity, is due to phase velocity dispersion within the waveguide.

In particular, the behavior of these additional "secondary magic conditions" could be likely attributed to phase delay accumulation due to group velocity dispersion effects on the comb pulse.

For this reason, the frequency matching the "main magic condition" has been called main frequency (or alternatively main wavelength), the others secondary frequencies.

Due to these additional secondary frequencies, Applicants have noted that cavity ring-down spectroscopy cannot be easily performed. Cavity ring down spectroscopy requires "switching off" the wavelength of interest which is interacting with the sample and measuring the decay. However multi-exponential decays corresponding to all resonant "secondary magic conditions" can mask ring-down events from the FMC. Moreover, secondary magic conditions are always coupled to the cavity even when the main magic condition is out of resonance, that is, when the cavity is unlocked. Therefore, in order to switch off only the main resonant frequency, an amplitude modulation is used. The main magic condition, i.e. the main wavelength or main frequency, is switched off by modulating the amplitude of the sidebands used for the PDH lock.

Before inputing the comb frequencies into the cavity waveguide, sidebands are added to the comb frequencies at all frequencies. More in detail, the comb frequencies are modulated in phase before they are coupled to the cavity. Each "teeth" of the comb therefore is split in the original carrier at the original frequency and in addition two sidebands having a distance from the carrier which depends on the frequency modulation chosen $\Delta v$. The chosen modulation is such that the location of the sidebands in frequency does not satisfy the "magic condition" (3) or (4). Therefore the sidebands are never a main or secondary frequency coupled into the cavity.

In addition to the two "lateral sidebands", higher harmonics are present at multiple of $\Delta v$, but the reasoning remains the same.

The phase modulation is used to "transfer" energy from the carrier to the sidebands. The higher the phase modulation depth, the smaller is the carrier in amplitude (the total energy is conserved) and the higher in amplitude the sidebands. Having therefore a strong enough modulation, the energy can be totally transferred to the sidebands, in this way "switching off" the carrier (which is the main frequency).

All the above is performed keeping the cavity locked to the frequency comb.

In particular the relative amplitude of the sidebands with respect to the carrier is rapidly changed from a first value to 100%, for example from 10% to 100%. When the amplitude is 10% the carriers of all comb frequency teeth belonging to both the main magic condition and the secondary magic conditions resonate with the cavity modes. Instead, when the relative amplitude is 100%, the main magic condition carrier power is totally transferred to its first and higher-order sidebands which are not resonant, while the second magic conditions carriers power is transferred to their sidebands which, on the contrary, are still resonant. This corresponds to On/Off turning of the main magic condition only.

In this way, the ring-down spectroscopy can be performed, because only the contribution of the "switching off" of the main frequency is evaluated. Preferably, evanescent wave spectroscopy is performed. As said, the cavity includes a waveguide which in turns includes a core and a cladding. Evanescent field exists at the core-cladding interface of the waveguide as the light propagates along the waveguide core. The sample that comes into this evanescent field of the guided mode propagation of the waveguide interacts with the light propagation and alters its intensity. This interaction of the evanescent field with the sample adjacent to it at the core-cladding interface provides the sensing mechanism. Evanescent wave absorbance can be measured and calculated by the modified Lambert-Beer law.

Evanescent field spectroscopy is preferred in case of liquid samples because of their strong absorption bands, which can easily saturate a standard spectrometer in the case of direct absorption through the liquid sample.

BRIEF DESCRIPTION OF THE DRAWINGS

The invention will be better understood in the following description with reference to the appended drawings, in which.

DETAILED DESCRIPTION OF A PREFERRED EMBODIMENT

Figure 2:
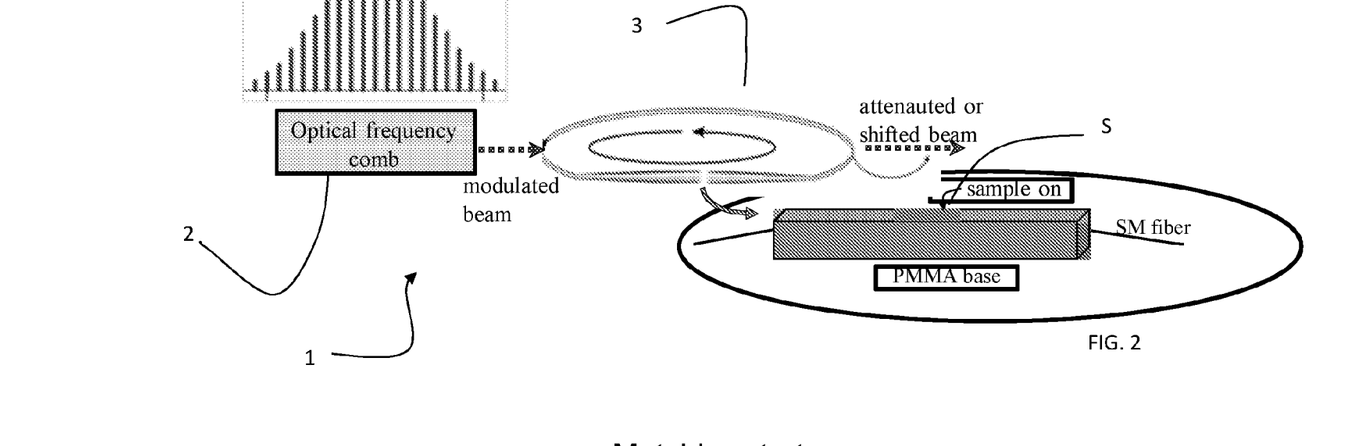
FIG. 2 is a schematic representation of the apparatus realized according to the invention.

With initial reference to FIG. 2, with 1 an apparatus to perform optical comb spectroscopy is globally indicated.

The apparatus includes a source of comb frequencies OFC (Optical Frequency Comb) 2 directed towards a waveguide resonant cavity 3. The comb frequencies having a frequency spacing RR are depicted in FIG. 1 (bottom line, where a "comb teeth" is indicated). The cavity 3 is a fiber loop cavity and in contact with it a sample S is arranged. The cavity has a plurality of cavity modes, depicted also in FIG. 1 (top line), which are separated by a frequency FSR. The sample S is preferably a liquid sample. Preferably, evanescent field spectroscopy is performed, therefore an evanescent-field access block (shown in the oval inlet) consisting of a side-polished single-mode optical fiber that allows interaction of the cavity evanescent field with a liquid sample is realized.

To make the OFC 2 resonating with the fiber loop 3, the repetition rate RR is tuned in order to match the magic condition of eq. (3) for the cavity 3, which is achieved when the comb teeth spacing is an integer multiple of the cavity FSR for a certain wavelength (see equation 3 and 4). This situation is schematically shown in FIG. 1 (matching strategy) where the "magic condition" is satisfied for a given RR and FSR. The RR is phase-locked to an external synthesizer.

However, the fiber cavity 3 acts as a dispersive element, i.e. as a fiber dispersion spectrometer (FDS). The whole OFC should resonate with the cavity 3 but, because of dispersion of the fiber, only a limited interval can be coupled. Therefore, for different wavelengths, the magic condition is satisfied by a slightly different RR. For each selected interval centered on a main wavelength (or frequency) the transmitted frequency is detected, for example by a suitable photodetector. In order to obtain a full spectrum of the sample S, the FDS operating wavelength is then preferably swept by tuning the repetition rate RR, for example using a radio-frequency synthesizer (RFS).

Figure 4:
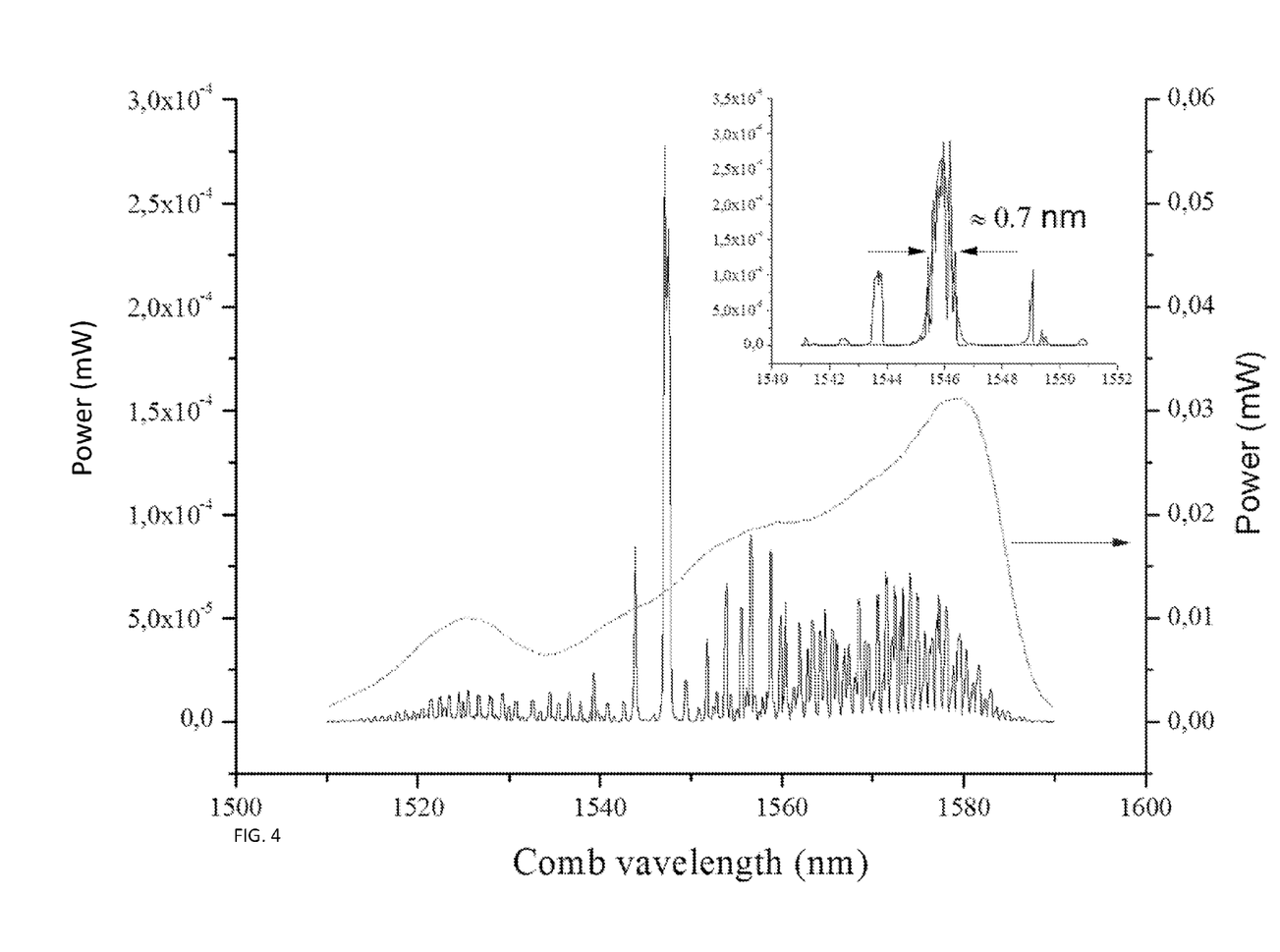
FIG. 4 is a graph of the spectral response of the apparatus of the invention centered at 1550 nm showing the main and secondary magic conditions. The resolution of the method of the invention can be appreciated in the magnified picture of the center peak in the inset.

In FIG. 4, a typical FDS spectral response is shown, as measured with an optical spectrum analyzer (OSA) around 1550 nm. The power envelope resumes the comb emission spectrum but a higher peak appears at the center. This corresponds to the primary comb resonance, called "main frequency", matching the "magic condition" at 1550 nm with a full width at half maximum (FWHM) of 0.7 nm (~300 teeth or comb frequencies). Also, a large population of narrower secondary magic conditions (SMCs) is visible at different wavelengths. The amplitude variation of the resonance peaks from the short-wavelength to the long-wavelength side originate from the spectral distribution of the comb power shown by the dotted line (right vertical axis).

SCRs are likely to be a consequence of group velocity.

In order to perform cavity ring down spectroscopy, the following is performed according to a preferred embodiment of the invention.

Preferably, before entering the fiber-loop cavity 3, sidebands, more preferably radio-frequency (RF) sidebands, are simultaneously superimposed to all comb teeth by a fiber coupled electro-optic phase modulator (EOM).

Due to the presence of SMCs, the comb frequency cannot be completely switched off by simply modulating the total incident light power as in most other systems. This problem is overcome here by switching off only the FMC with amplitude modulation of PDH sidebands via the EOM.

Figure 6:
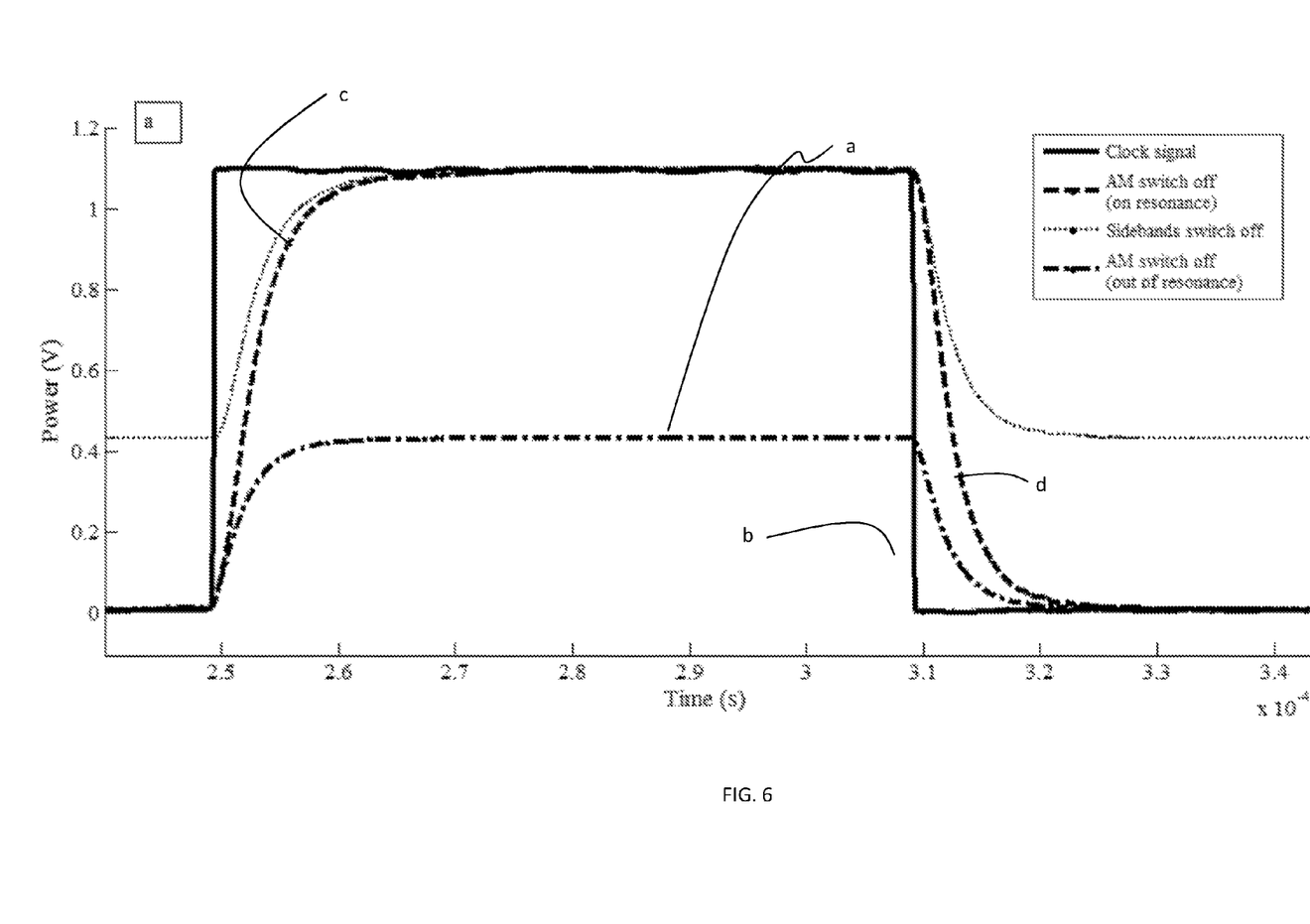
FIG. 6 is a graph showing cavity pulse response as observed for different kinds of modulations.

In theory, only the group of teeth corresponding to the spectral interval selected by the PCR resonates within the cavity once the system is locked. Due to the presence of the SCRs, however, the PFC cannot be completely switched off by power modulation of the incident light beam as usually done in many other systems. In fact, the exponential decay corresponding to several resonant SCRs can mask the ring-down events from the PCR. The SCRs are always coupled to the cavity even when the PCR is out of resonance, i.e. when the cavity is unlocked. This particular behavior is illustrated in FIG. 6. The ring-down curves are first obtained by switching off the OFC beam through an electro-optic amplitude modulator. The d curve (dashed curve in FIG. 6) corresponds to the ring-down when the cavity is locked to the PCR, with an overlap of PCR and SCRs decays. The a curve (dot-dashed curve in FIG. 6) is the ring-down measured when the PCR is out of resonance (cavity unlocked): the residual decay is due only to SCRs. The b (solid) curve is the modulation clock signal. Therefore, during the PCR wavelength scan, there are always spurious exponential decays at other wavelengths due to the SCRs. Always resonant SCRs may compromise the correct operation of the spectrometer.

This problem is overcome by switching off only the PCR by deep amplitude modulation of the PDH sidebands using the EOM.

For this purpose, the relative amplitude of the sidebands with respect to the carrier is rapidly changed from 10% to 100%. When the amplitude is 10%, the carriers of all OFC teeth belonging to both the PCR and the SCRs resonate with the cavity modes. Instead, when the relative amplitude is 100%, the PCR carrier power is totally transferred to its first and higher-order sidebands (FIG. 5) which are not resonant, while the SCRs carriers power is transferred to their sidebands which, on the contrary, are still resonant. This corresponds to On/Off turning of the PCR only. In fact, as shown in FIG. 6, the upper exponential curve does not decay down to zero but to a plateau corresponding to the always-resonant SCRs (c line, thin solid curve). In other words, the c curve is the ring-down signal when the OFC beam is switched off by amplitude modulation of sidebands, where the exponential curve decays to a horizontal asymptote.

Figure 5:
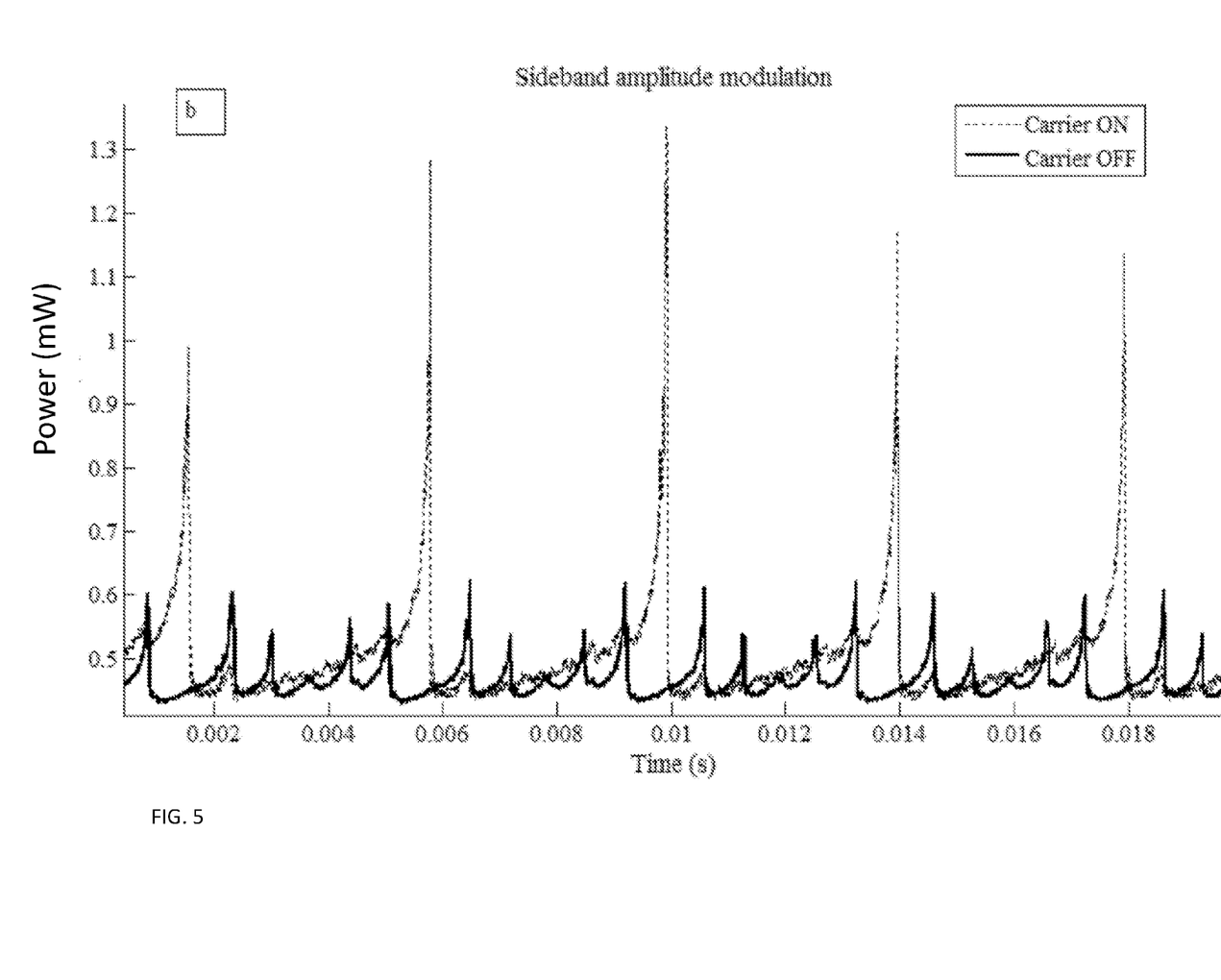
FIG. 5 is a graph showing the comb fast switching action by deep sideband amplitude modulation along a cavity length scan across the resonances.

Coming back to FIG. 5, the dotted line represents the transmitted spectrum when the carrier is ON and the PCR and SCR are all resonating in the cavity. The solid line represents the carrier OFF: the comb fast switching by deep sideband amplitude modulation is shown along a cavity length scan across the resonances.

Figure 8:
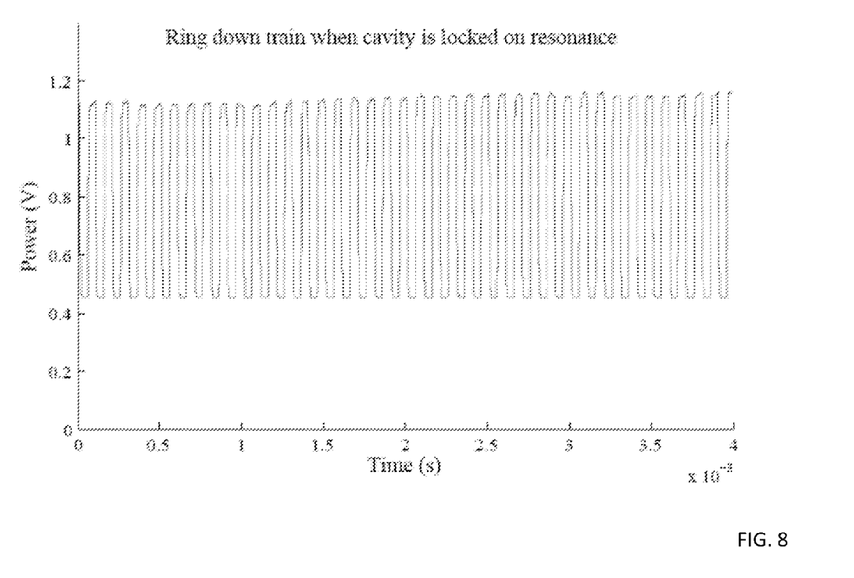
FIG. 8 is a graph showing the ring-down pulse train when the cavity is locked to the comb.

A plurality of ring-down decays such as the one shown in FIG. 6 curve c is represented in FIG. 8: this figure shows a ring down pulse train when the cavity is locked to the comb on resonance, an acquisition run over several square pulses.

Figure 7:
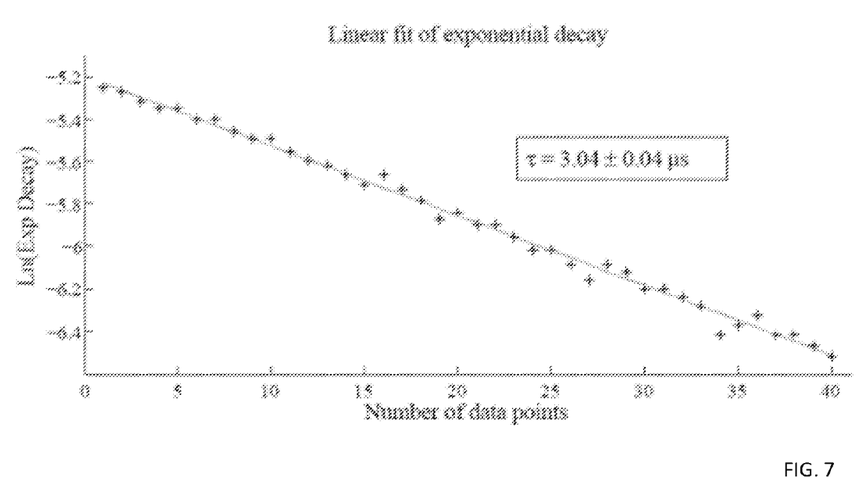
FIG. 7 is a graph showing the least-square fit of a linearized cavity-decay event.

As generally performed in ring-down spectroscopy, a least-square exponential fit of this decay is performed to measure the intra-cavity loss and thus to retrieve the changes caused by evanescent-wave interaction with an absorbing liquid on the EAB (FIG. 7). From the rms fluctuation of 100 recordings, in the same experimental conditions, a rms deviation over repeated ring-down measurements of 0.04 µs is obtained. Each measured value results from the average of the fit estimates obtained from multiple decay events.

EXAMPLE

Figure 3:
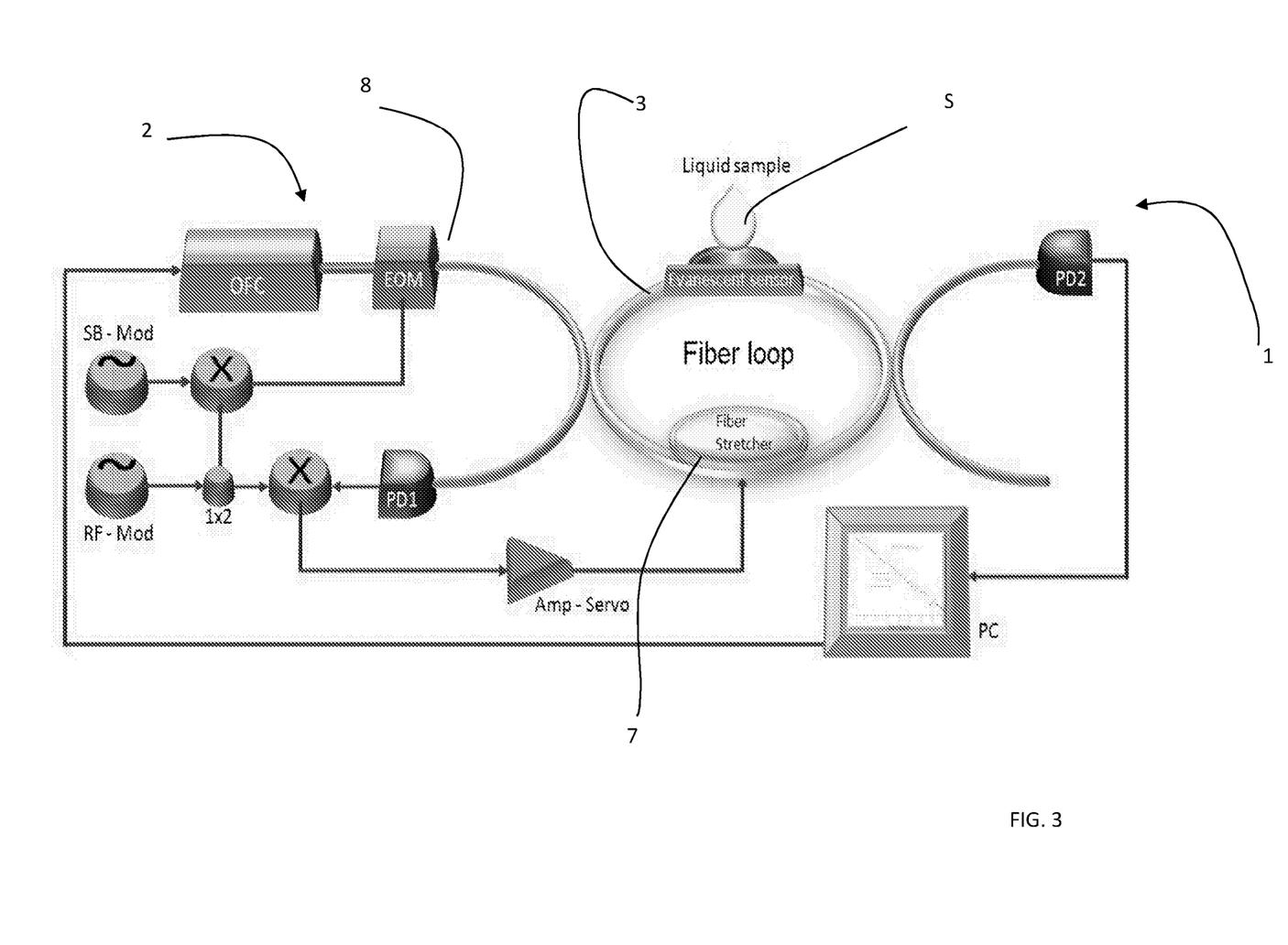
FIG. 3 is a more detailed representation of the apparatus of FIG. 2.

Reference is now made to FIG. 3 where a more detailed layout of the apparatus of the invention is sketched.

The sensing element, an evanescent-field access block (EAB) 3, consists of a single-mode optical fiber (SMF28 Corning) which is side-polished down to the core along a short length (~1 mm): the resulting D-shaped fiber allows interaction of the cavity evanescent field with a chemical sample S nearby. The resulting D-shaped fiber allows interaction of the cavity evanescent field with the sample S over a 1 mm×0.125 mm area. Using absorption from known liquid species, the estimated effective EAB interaction length, rescaled by the actual penetration depth of the evanescent field, is of about 30 µm. The EAB is inserted into a 20.4-m fiber-loop cavity 3, whose length is finely controlled by a custom-built piezoelectric fiber-stretcher FS 7. The cavity 3 has a free spectral range (FSR) of 10 MHz and a finesse around 200, corresponding to a linewidth of 50 kHz.

The interrogating optical frequency comb (OFC) source 2 is a 80-fs pulsed modelocked erbium-fiber laser (Menlo Systems FC1500) with an average output power of 30 mW in the region from 1515 nm to 1585 nm and a RR of 250 MHz. The repetition rate (RR) is phase locked to an external radio-frequency synthesizer (RFS) oscillating at about 250 MHz, which can be finely tuned by an external analog signal. Wide excursion of the RR can be achieved by changing the laser-comb internal stepped motor. The OFC spectral coverage is also expanded by a non-linear fiber that generates supercontinuum emission spanning one octave, from 1.05 to 2.1 µm, with an average power of 100 mW but still preserving the characteristic comb teeth spectrum.

The OFC light is injected into the cavity 3 and collected through 0.6-% fiber couplers. The near-infrared beam passes through a fiber-coupled electro-optic modulator EOM 8 to generate sidebands before entering the cavity. The apparatus also includes phase modulation to switch the beam off (SB-Mod) and phase modulation for PDH locking (RF-Mod). A photodiode (PD) is used for detection of the transmitted light and a personal computer (PC) is used for the elaboration of data. Amp-Servo: amplifier and locking servo electronics.

The system is all-fiber made without any free-space gap.

In order to match the magic condition for the cavity 3, the repetition rate RR is tuned to be 25 times the FSR. In principle, in this condition the whole OFC should resonate with the cavity but, because of fiber dispersion, only a limited wavelength interval can be effectively coupled. Hence the fiber cavity itself acts as a dispersive element (FDS) thus providing spectral analysis of the recorded signals. In the present case, the resolution is about 0.7 nm, but it could be readily improved increasing the fiber-loop length or the finesse, also improving the spectrometer sensitivity. A fixed relation exists between the RR radiofrequency and the FDS center: the operating wavelength is calibrated by tuning the RR synthesizer (RFS).

As shown in FIG. 4, many secondary resonances are visible. Considering a fiber cavity with a length of about 20 m, for the present OFC the magic condition of eq. (4) is obtained to be L=20.4 m and RR=249000 MHz, for m=25 and n=1.46 (at 1550 nm). For fixed L and RR, the next magic condition (m=26) is obtained from Eq. 1 for n=1.9, which is not possible in the presence of group velocity dispersion. SCRs could be likely attributed to group velocity dispersion (GVD) effects on the OFC pulse. Actually, only the teeth included in the spectral interval selected by the FDS (FMC) resonate within the cavity and can be used for ring-down spectroscopy. Due to the presence of SCRs, the OFC cannot be completely switched off by simply modulating the total incident light power as in most other systems. The OFC is phase modulated before entering the fiber-loop. Radio frequency (RF) sidebands at about 1 MHz are simultaneously superimposed to all comb teeth by the EOM. A Pound-Drever-Hall (PDH) scheme allows frequency locking of the cavity modes to the OFC by means of a piezo-actuated fiber stretcher, as shown in the schematic of the experimental set-up (FIG. 3). Error signals centered on the cavity modes are obtained by demodulation of the cavity reflection (PD1) in a RF mixer at the sideband frequency. CRDS measurements are performed from the signal detected through the second fiber coupler (PD2). Only the group of teeth corresponding to the spectral interval selected by the PCR resonates within the cavity once the system is locked.

Then liquid samples are placed on the EAB sensor and multiple time domain CRDS measurements are performed from the signal detected through the second fiber coupler PD2.

The performance of the method of the invention was assessed in a test experiment with liquid samples containing polyamines exhibiting strong absorption bands in the near infrared due to overtone vibrations. Owing to the strength of polyamine bands in the near infrared, absorption would rapidly saturate if pure compounds were used. On the other hand, the modified confinement conditions of the side-polished fiber give the EAB a characteristic response to external refractive index (RI): both changes of its real and imaginary parts cause optical loss, the cavity being more sensitive to sample absorption when the RI approaches the fiber group index (critical value). Therefore, all the samples are properly diluted with buffer solutions (heavy water) and their RI is adjusted to be close to the critical condition. In this proof of concept, heavy water was used to minimize the overlap of polyamine bands with absorption due to the remainder of the mixture. The spectrometer operation is fully automated. During RR steps (FDS), the fiber cavity remains locked to the OFC teeth while a LabVIEW™ program controls both the RFS for fine tuning of the PCR and the PDH signal to ensure a correct frequency-lock operation (see FIG. 3). Simultaneously, the program acquires intracavity power data and performs ring-down time retrievals. The PCR wavelength scan is accurately calibrated from the instantaneous RR values without need for any additional device. Each measured value results from the average of the fit estimates on 100 decay events (see FIG. 7): from 100 repeated ring-down measurements in the same experimental conditions, a mean ring-down time $\tau=3.04$ μs is obtained with a standard error of 0.004 μs (standard deviation divided by the square root of the number of samples). Using this value, a minimum detectable single-pass absorbance of $3\times10^{-5}$ for each spectral point is estimated, i.e. $1\times10^{-6}$ Hz$^{-1/2}$ considering an effective detection bandwidth of $$\frac{1}{2\pi\tau N} \approx 524 \text{ Hz}$$

(N numer of averaged acquisitions). This figure of merit is a factor 200 above the shot-noise limit estimated for the incident optical power in each PCR (~4 μW), but it leads to a high sensitivity level if compared to other laser-based fiber-cavity systems. This value translates into a noise-equivalent absorption coefficient of $3\times10^{-4}$ cm$^{-1}$/√Hz per spectral point, considering the effective evanescent-wave interaction length of the sensor of the present invention (30 μm). In addition, thanks to the OFC, the sensor is capable of providing also information on the absorption spectrum over a wide wavelength range. The whole procedure lasts about 120 s for recording a full spectrum, however the time necessary for recording each spectrum can be easily made as short as 20 ms (i.e. 2 s with 100-sample real time average).

Figure 9A:
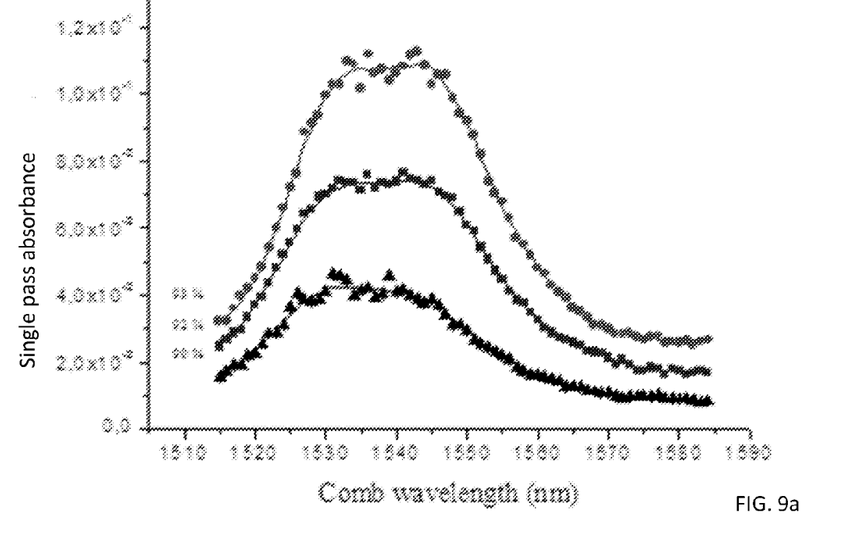
FIGS. 9a and 9b represent evanescent-wave absorption spectra obtained by the method of the invention with a sample containing ethylenediamine (EDA) diluted in $D_2O$ at different concentrations (from 90 to 93%), and a sample containing tetraethylenepentamine (TEPA) diluted in $D_2O$ at different concentrations (from 50 to 62%), respectively.
Figure 9B:
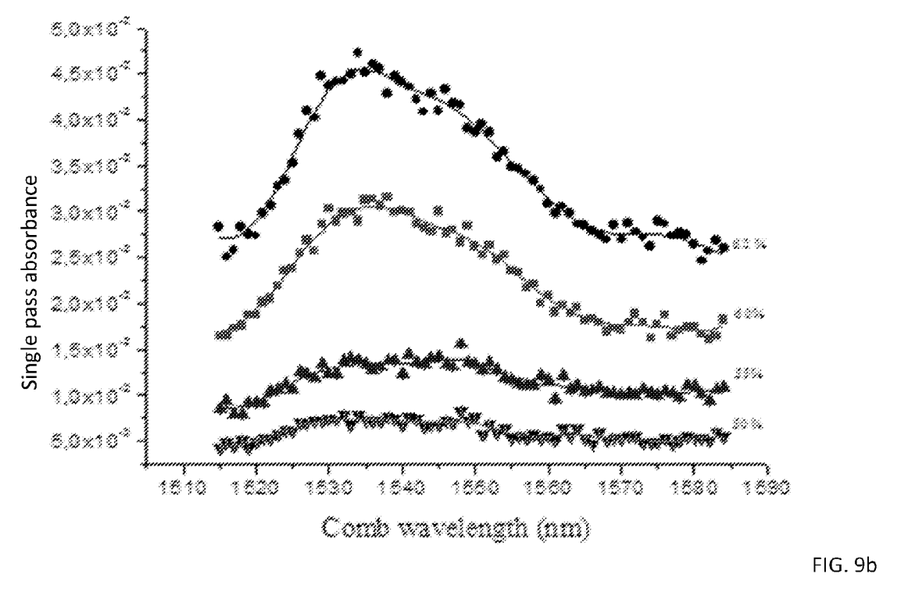

In FIG. 9a, ring-down measurements along a fast scan of the FDS around an absorption band of ethylenediamine (EDA) using the direct Er-laser comb emission in the telecommunication range (1515-1585 nm) are shown. The result is in good agreement with an FTIR spectroscopic database. These recordings are obtained with a drop of solution prepared from EDA in D$_2$O at volume concentrations varying around 90%. The data have been further filtered by 2-points adjacent averaging. From the rms fluctuation of 100 repeated ring-down measurements in the same experimental conditions, we estimated a minimum detectable value of single-pass absorbance in the order of $6\times10^{-4}$. The absorption spectra of other liquid polyamines is also measured. FIG. 9b shows the evanescent-wave absorption spectrum of a sample containing tetraethylenepentamine (TEPA) diluted in D$_2$O at variable concentrations.

Figure 10:
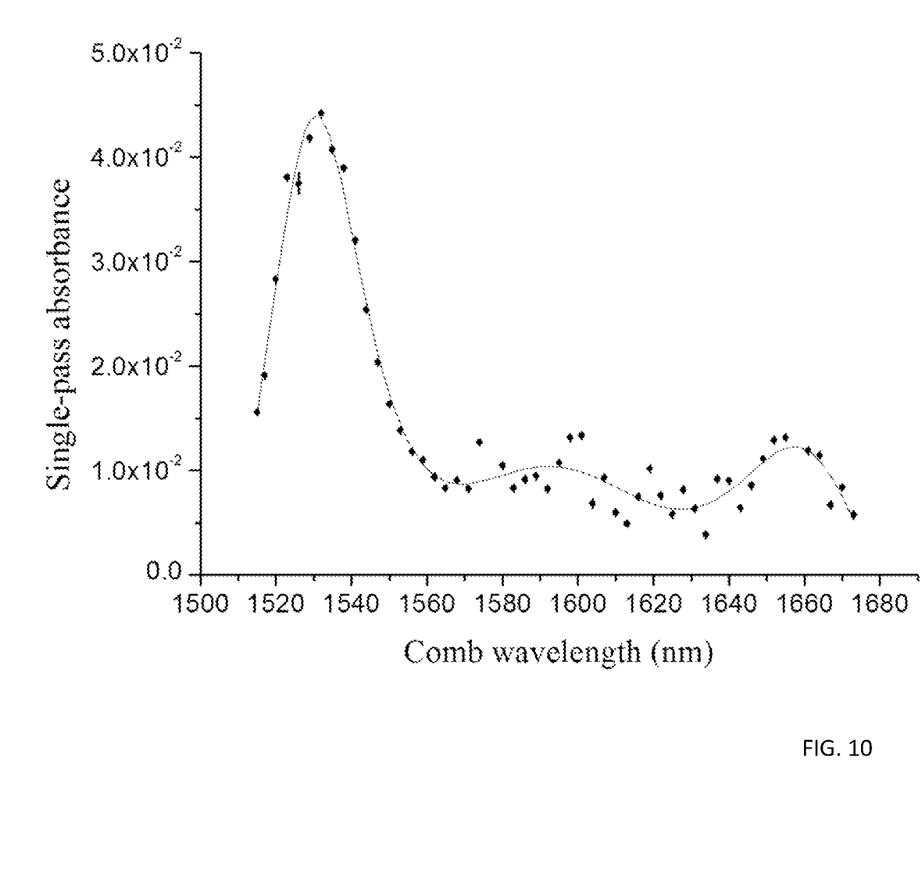
FIG. 10 is a graph showing absorption bands observed using the extended comb with a 90-% EDA concentration at a lower spectral resolution (~3 nm). A three-Lorentian curve function is fitted to the experimental spectrum (continuous line) pointing out two side bumps. The bandwidths are in the order of 20 nm.

An extended EDA spectrum from 1515 nm to 1675 nm has been finally recorded at a slightly lower resolution using the spectrally broadened OFC beam, as shown in FIG. 10. The overall decrease and the large excursions of the comb power along the extended emission range add some instabilities to the frequency-locking loop thereby causing a degradation of the signal-to-noise ratio. The presence of bumps towards longer wavelengths could originate from weaker absorption bands or be a consequence of the evanescent-wave interaction on the fiber sensor.

FIG. 9b shows evanescent-wave absorption spectra obtained with a sample containing tetraethylenepentamine (TEPA) diluted in D2O at concentrations from 50 to 62%.

Using the method and the apparatus of the invention, detection of liquid polyamines dissolved in water is obtained, via a comb-based, evanescent wave fiber spectrometer covering a full spectral range of about 160 nm that comprises different absorption features. Cavity ring-down spectroscopy enhances the detection sensitivity while fiber dispersion provides spectral reconstruction. In fact, as opposed to previous systems, where dispersion causes strong bandwidth limitations, strong GVD effects due to the fiber cavity can be exploited for direct analysis of absorption spectra, without using any additional element. At the same time, secondary magic conditions are also induced by intra-cavity GVD, but their effect on the signals obtained in the method of the invention is efficiently suppressed thanks to sideband amplitude modulation that allows to selectively switch off the fundamental resonance between the comb and the cavity. The detection performance, as well as the spectral coverage of the spectrometer, can be further improved by increasing the Er-laser output power before the fiber broadening stage. Moreover, thanks to the small-size probe and the fully optical-fiber-based set-up, such sensors lend themselves to be integrated in micro-opto-fluidic systems as miniature spectrometers.

The invention claimed is:

1. Method for performing frequency comb spectroscopy, the method comprising:
   arranging a waveguide optical cavity (3) having a plurality of cavity mode frequencies with a cavity mode frequency spacing (FSR), said waveguide optical cavity being dispersive so that said frequency spacing of the cavity modes is wavelength dependent;
   arranging a sample (S) with respect to the waveguide optical cavity (3) so that the sample is capable of absorbing light travelling into the waveguide optical cavity;
   coupling pulsed light coming from a light source (1) into the waveguide optical cavity (3), the source light including source comb frequencies (OCF) with a source frequency spacing (RR), the coupled light including an interval of frequencies centered on a main frequency of said comb frequencies due to cavity dispersion;
   locking the waveguide optical cavity to the frequency comb at said main optical frequency;
   detecting transmitted cavity frequencies;
   determining absorption by said sample (S) of said main optical frequency from the detected transmitted frequencies,
   changing the cavity mode frequency (FSR) spacing or the source frequency spacing (RR);
   coupling the pulse light to the waveguide optical cavity (3), the coupled light including an interval of frequencies centered on a second main frequency of said comb frequencies due to cavity dispersion;
   locking the waveguide optical cavity to the frequency comb at said second main optical frequency;
   detecting transmitted cavity frequencies;
   determining absorption by said sample of said second main optical frequency from the detected transmitted frequencies.

2. The method of claim 1, wherein said locking the frequency comprises using a Pound-Drever-Hall technique.

3. The method of claim 1, wherein said changing the cavity mode frequency (FSR) spacing or the source frequency spacing (RR) is repeated till the whole frequency range of interest is covered.

4. The method according to claim 1, wherein determining absorption by said sample (S) of said main optical frequency from the detected transmitted frequencies comprises determining a single line of the absorption spectrum.

5. The method of claim 1, wherein said frequency comb spectroscopy comprises a cavity ring down spectroscopy scheme.

6. The method according to claim 5, comprising the steps of:
   generating sidebands having a frequency not resonant with said cavity (3);
   superimposing said sidebands to said comb frequencies in said interval of frequencies; amplitude-modulating said sidebands.

7. The method of claim 6, wherein said amplitude modulating of said sidebands comprises changing the amplitude of the sidebands with respect to the carrier of the main frequency from a first value to about 100%.

8. The method of claim 7, comprising, after changing the amplitude of said sidebands to 100%, measuring the ring-down time of the decay of the carrier of the main frequency.

9. The method according to claim 1, wherein said changing the cavity mode frequency spacing or the source frequency spacing comprises tuning the source comb frequencies (RR).

10. The method according to claim 1, wherein arranging a sample (S) with respect to the waveguide optical cavity (3) comprises:
    arranging said sample so that it interacts with an evanescent field of said cavity modes.

11. An apparatus for frequency comb spectroscopy, comprising:
    a waveguide optical cavity (3) having a plurality of cavity mode frequencies with a cavity mode frequency spacing (FSR), said waveguide optical cavity being dispersive so that said frequency spacing of the cavity modes is wavelength dependent;
    a sample (S) arranged with respect to the waveguide optical cavity (3) so that the sample is capable of absorbing light travelling into the waveguide optical cavity;
    a light source (1) capable of emitting source comb frequencies (OFC) with a source frequency spacing (RR);
    coupling means to couple the source comb frequencies to the waveguide optical cavity, the coupled light including an interval of frequencies centered on a main frequency of said interval of comb frequencies due to cavity dispersion;
    a locking device to lock the waveguide optical cavity to the frequency comb at said main optical frequency;
    a detector (PD2) for detecting transmitted cavity frequencies and determining absorption by said sample (S) of said main optical frequency from said detected transmitted frequencies;
    a tuner to change the cavity mode frequency spacing or the source frequency spacing.

12. The apparatus according to claim 11, wherein said source comprises a comb laser source.

13. The apparatus according to claim 11, wherein said light source (1) emits near-infrared radiation.

14. The apparatus according to claim 11, wherein said waveguide optical cavity (3) comprises a waveguide loop.

15. The apparatus according to claim 11, wherein said waveguide optical cavity is a single mode cavity.

16. The apparatus according to claim 11, wherein said sample comprises a liquid sample.

17. The apparatus according to claim 11, wherein the dispersion of said waveguide cavity is such that group velocity dispersion (GVD) of said waveguide cavity (3) is higher than 0.0074 ps2/m at the main frequency.

* * * * *